United States Patent
Takezaki et al.

(10) Patent No.: US 9,941,817 B2
(45) Date of Patent: Apr. 10, 2018

(54) ULTRASONIC TRANSDUCER AND ULTRASONIC DIAGNOSTIC EQUIPMENT USING THE SAME

(75) Inventors: Taiichi Takezaki, Tachikawa (JP); Shuntaro Machida, Kokubunji (JP)

(73) Assignee: HITACHI, LTD., Tokyo (JP)

( * ) Notice: Subject to any disclaimer, the term of this patent is extended or adjusted under 35 U.S.C. 154(b) by 1054 days.

(21) Appl. No.: 13/879,439

(22) PCT Filed: Oct. 13, 2011

(86) PCT No.: PCT/JP2011/073582
§ 371 (c)(1),
(2), (4) Date: Jun. 4, 2013

(87) PCT Pub. No.: WO2012/050172
PCT Pub. Date: Apr. 19, 2012

(65) Prior Publication Data
US 2013/0241345 A1   Sep. 19, 2013

(30) Foreign Application Priority Data
Oct. 15, 2010   (JP) ................................. 2010-232618

(51) Int. Cl.
*H02N 1/08* (2006.01)
*A61B 8/00* (2006.01)
(Continued)

(52) U.S. Cl.
CPC ............. *H02N 1/08* (2013.01); *A61B 8/4483* (2013.01); *A61B 8/4494* (2013.01);
(Continued)

(58) Field of Classification Search
USPC ...................................................... 367/104
See application file for complete search history.

(56) References Cited

U.S. PATENT DOCUMENTS

2002/0123685 A1*   9/2002   Miwa .................. G01S 7/52026
600/437
2003/0067249 A1*   4/2003   Lockwood ............ B06B 1/0622
310/324
(Continued)

FOREIGN PATENT DOCUMENTS

JP   2002-191180   7/2002
JP   2006-20313   1/2006
(Continued)

*Primary Examiner* — Isam A Alsomiri
*Assistant Examiner* — Amie M Ndure
(74) *Attorney, Agent, or Firm* — Baker Botts L.L.P.

(57) ABSTRACT

High transfer sound pressure and high reception sensitivity are realized, and reliability is improved in terms of long term operation, in a capacitive detector-type ultrasonic transducer (CMUT). The ultrasonic transducer, which has a lower electrode (201), a hollow portion (202) that is formed on the lower electrode and surrounded by insulating films (209, 208), an upper electrode (205) that is formed on the hollow portion, and a plurality of insulating film projections (204) that are formed in the hollow portion (202), comprises a plurality of rigid members (203) that are formed on the hollow portion, either the lower electrode (201) and/or the upper electrode (205) is disposed in a position that does not overlap with the insulating film projections (204) when viewed from the upper surface by carving out the portion that overlaps with the insulating film projections (204), and the respective rigid members (203) are disposed such that a region is present that overlaps with the insulating film projections (204) when viewed from the upper surface.

20 Claims, 11 Drawing Sheets

(51) Int. Cl.
    *B06B 1/02*     (2006.01)
    *G01N 29/24*     (2006.01)
    *H04R 19/04*     (2006.01)

(52) U.S. Cl.
    CPC ....... *B06B 1/0292* (2013.01); *G01N 29/2406* (2013.01); *H04R 19/04* (2013.01)

(56) References Cited

U.S. PATENT DOCUMENTS

| | | | |
|---|---|---|---|
| 2004/0085858 A1 | 5/2004 | Khuri-Yakub et al. | |
| 2005/0228285 A1 | 10/2005 | Huang et al. | |
| 2006/0004289 A1* | 1/2006 | Tian | B06B 1/0292 600/459 |
| 2007/0052093 A1* | 3/2007 | Machida | B06B 1/0292 257/735 |
| 2009/0208037 A1* | 8/2009 | Zhe | H04R 7/20 381/174 |
| 2009/0301200 A1* | 12/2009 | Tanaka | B06B 1/0292 73/603 |
| 2009/0322181 A1 | 12/2009 | Machida et al. | |
| 2010/0254222 A1* | 10/2010 | Huang | B06B 1/0292 367/181 |
| 2010/0280381 A1* | 11/2010 | Madore | G01S 7/5209 600/447 |

FOREIGN PATENT DOCUMENTS

| | | |
|---|---|---|
| JP | 2006-516368 | 6/2006 |
| JP | 2007-74263 | 3/2007 |
| JP | 2009-100460 | 5/2009 |
| WO | WO 2007/046180 A1 | 4/2007 |

\* cited by examiner

ULTRASONIC TRANSDUCER AND ULTRASONIC DIAGNOSTIC EQUIPMENT USING THE SAME

TECHNICAL FIELD

The present invention relates to an ultrasonic transducer and an ultrasonic diagnostic equipment using the ultrasonic transducer. More particularly, the present invention is concerned with an ultrasonic transducer manufactured using a micro-electro-mechanical systems (MEMS) technology.

BACKGROUND ART

Ultrasonic transducers that transmit or receive an ultrasonic wave are employed in diagnosis of a tumor or the like in a human body, nondestructive testing of a structure, sensing of the velocity of a fluid, or the like.

Ultrasonic transducers that utilize vibrations of a piezoelectric entity have been used in the past. With recent advancement of the MEMS technology, a capacitive micromachined ultrasonic transducer (CMUT) having a vibration unit fabricated on a silicon substrate is being developed in earnest.

For example, patent literature 1, patent literature 2, and patent literature 3 have disclosed improvement of reliability in activities of a CMUT. Patent literature 4 has disclosed a method of controlling a center frequency and a bandwidth offered by the CMUT.

CITATION LIST

Patent Literature

Patent Literature 1: U.S. Patent Application Publication No. 2005/0228285
Patent Literature 2: U.S. Patent Application Publication No. 2009/0322181
Patent Literature 3: Japanese Patent Application Laid-Open No. 2007-74263
Patent Literature 4: International Publication No. 2007-046180

SUMMARY OF INVENTION

Technical Problem

The patent literature 1 has disclosed a structure in which: projections of an insulating film jutting out to a hollow portion of a CMUT are formed; and even when a direct-current (dc) voltage or alternating-current (ac) voltage equal to or higher than a collapse voltage is applied, although the projection undersurfaces come into contact with the hollow portion bottom, a membrane undersurface does not come into contact with the hollow portion bottom. However, since the projections are sandwiched between upper and lower electrodes, charge injection into the insulating film of the projections cannot be avoided.

In contrast, the patent literature 2 describes a structure in which portions of an electrode are pierced for fear fields in which a membrane undersurface comes into contact with a hollow portion bottom may be sandwiched between upper and lower electrodes. In the case of the structure, since the electric field strength in a membrane insulating film in the contact fields is decreased, charge injection can be avoided. However, the area of layered portions of the upper and lower electrodes diminishes accordingly. This invites a rise in a driving voltage for a CMUT or degradation in receiving sensitivity.

In the patent literature 3, projections of an insulating film jutting out to a hollow portion are not sandwiched between upper and lower electrodes. Even in this case, by the same reason as the foregoing one, a rise in a driving voltage for a CMUT or degradation in receiving sensitivity is invited.

In the patent literature 4, a membrane is provided with rigid members in order to adjust the rigidness of the entire membrane. Thus, the center frequency and bandwidth offered by a CMUT are controlled. However, introduction of the rigid members brings about a rise in a driving voltage. How to ensure reliability in device activities becomes an object to be accomplished.

Accordingly, an object of the present invention is to provide an ultrasonic transducer which is a CMUT that has projections jutted out to a hollow portion and has at least one of an upper electrode and lower electrode located at a position at which the electrode is not layered over the projections when viewed from the upper surface, and an ultrasonic diagnostic equipment employing the CMUT. Herein, a voltage margin between the instant projection undersurfaces come into contact with a hollow portion bottom and the instant a membrane undersurface comes into contact with the hollow portion bottom is preserved, charge injection into a membrane insulating film is suppressed, and a high transmission sound pressure and a highly reliable structure are realized.

Solution to Problem

In order to address the foregoing problem, an ultrasonic transducer of the present invention includes a lower electrode, a hollow portion formed over the lower electrode and enclosed with an insulating film, an upper electrode formed over the hollow portion, and plural projections of the insulating film formed in the hollow portion. The ultrasonic transducer has plural rigid members formed over the hollow portion. At least one of the lower electrode and upper electrode has portions thereof, which are layered over the projections of the insulating film, pierced, so that the electrode is located at a position at which the electrode is not layered over the projections of the insulating film when viewed from the upper surface. The rigid members are disposed so that they have fields which are layered over the respective projections of the insulating film when viewed from the upper surface.

In the ultrasonic transducer of the present invention, the rigid members are beam members. A membrane including the insulating film, upper electrode, and beam members may have a portion thereof, in which the beam members are disposed, made thicker than a portion thereof, in which the beam members are not disposed, by the thickness of the beam members.

The ultrasonic transducer of the present invention includes an upper insulating film formed to cover the upper electrode and hollow portion. The beam members may be disposed over the upper insulating film.

The ultrasonic transducer of the present invention includes an upper insulating film formed to cover the upper electrode and hollow portion. The beam members may be embedded in the upper insulating film.

In the ultrasonic transducer of the present invention, the rigid members may be members exhibiting a higher Young's modulus than the membrane, which includes the insulating film, upper electrode, and beam members, does.

The ultrasonic transducer of the present invention includes an upper insulating film formed to cover the upper electrode and hollow portion. The members of the higher Young's modulus may be embedded in the upper insulating film.

In the ultrasonic transducer of the present invention, the members of the higher Young's modulus may be formed by embedding a metallic material such as tungsten or a ceramic material such as alumina.

In the ultrasonic transducer of the present invention, the members of the higher Young's modulus may be formed by reforming the upper insulating film through ion implantation.

In the ultrasonic transducer of the present invention, the rigid members may be disposed so that the centers thereof coincide with the centers of the projections of the insulating film when viewed from the upper surface.

In the ultrasonic transducer of the present invention, the rigid members may be disposed so that one rigid member is layered over plural projections of the insulating film.

In the ultrasonic transducer of the present invention, the projections of the insulating film may be disposed over the top of the hollow portion.

In the ultrasonic transducer of the present invention, the projections of the insulating film may be disposed over the bottom of the hollow portion.

In the ultrasonic transducer of the present invention, the plural projections of the insulating film and the plural rigid members may be equidistantly disposed when viewed from the upper surface.

In the ultrasonic transducer of the present invention, the hollow portion may be circular or polygonal when viewed from the upper surface.

In the ultrasonic transducer of the present invention, the projections of the insulating film may be circular or polygonal when viewed from the upper surface.

In the ultrasonic transducer of the present invention, the rigid members may be circular, cruciform, or polygonal when viewed from the upper surface.

An ultrasonic diagnostic equipment of the present invention includes any of the foregoing ultrasonic transducers and a bias unit.

Advantageous Effects of Invention

According to the present invention, a capacitive micromachined ultrasonic transducer (CMUT) can realize a high transmission sound pressure and high receiving sensitivity, and improve reliability in long-term driving.

DESCRIPTION OF EMBODIMENTS

Referring to the diagrams, embodiments of the present invention will be described below.

In the embodiments to be described below, for convenience' sake, plural sections or embodiments will be dividedly described when needed. Unless explicitly mentioned, the sections or embodiments are not unrelated to one another, but one of the sections or embodiments is part of any other one or a variant of all of the others, or is cited in order to detail or supplement any other section or embodiment. In the embodiments to be described below, when the number of elements (the number of pieces, a numerical value, a quantity, a range, or the like) is stated, unless the number of elements is explicitly specified or is in principle apparently limited to a specific value, the number of elements is not limited to the specific value but may be equal to or larger than the specific value or may be equal to or smaller than the specific value. Further, in the embodiments to be described below, unless components (encompassing element steps) are explicitly specified or thought to be in principle apparently essential, the components are not always needed. Likewise, in the embodiments to be described below, when the shape of a component or the like or a positional relationship between components is stated, unless the shape or positional relationship is explicitly specified or is not in principle apparently thought to be correct, the shape encompasses a substantially approximate or analogous shape. The same applies to the numerical value or range. Even in plan views, hatching may be performed for a better understanding.

In the embodiments to be described below, in a capacitive micromachined ultrasonic transducer (CMUT), an object of suppressing charge injection to a membrane insulating film or a decrease in a dielectric strength by expanding a voltage margin between a state in which the undersurfaces of projections jutting out to a hollow portion come into contact with the hollow portion bottom and a state in which a membrane undersurface comes into contact with the hollow portion bottom is accomplished with such a disposition that at least parts of rigid members or high-Young's modulus members which are included in the membrane are layered over the projections jutting out to the hollow portion when the CMUT is viewed from the upper surface.

Embodiment 1

Figure 3:
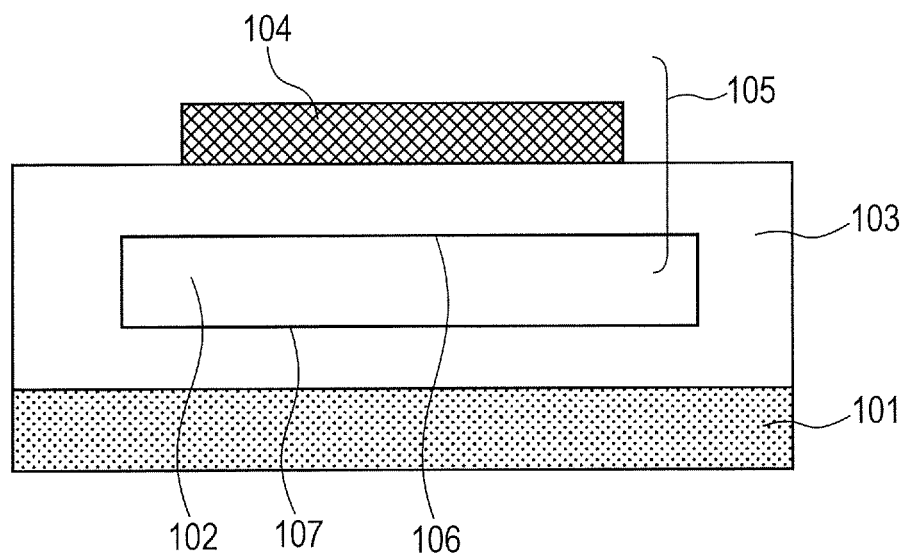
FIG. 3 is a cross-sectional diagram of a CMUT which the present inventor et al. have discussed.

Referring to FIG. 3, a fundamental structure of a CMUT and activities thereof will be described below. A hollow portion 102 enclosed with an insulating film 103 is formed in an upper layer of a lower electrode 101. An upper electrode 104 is disposed over the hollow portion 102 with the insulating film 103 between them. When a dc voltage and ac voltage are convoluted between the upper electrode 104 and lower electrode 101, electrostatic force works between the upper electrode 104 and lower electrode 101. A membrane 105 including the insulating film 103 and upper electrode 104 over the hollow portion 102 is vibrated at the frequency of the applied ac voltage, whereby an ultrasonic wave is originated.

For receiving, when the dc voltage alone is applied between the upper electrode 104 and lower electrode 101, the membrane 105 is vibrated due to the pressure of an ultrasonic wave having reached the surface of the membrane 105. This causes the distance between the upper electrode 104 and lower electrode 101 to vary. Eventually, the ultrasonic wave can be detected as a change in a capacitance.

One of the most significant features of an ultrasonic transducer is that a signal-to-noise ratio is high. For example, when it says that an ultrasonic diagnostic equipment or flaw inspection apparatus offers a high signal-to-noise ratio, it means that image quality is sharp. The high signal-to-noise ratio is significant in terms of the performance of the equipment or apparatus. In order to raise the signal-to-noise ratio to be offered by a CMUT, a capacitance change at a receiving time should be increased. The capacitance change may be increased by increasing the number of CMUTs or expanding the area of the CMUT. In this case, the size of the transducer gets larger. Therefore, it is necessary to increase the capacitance change per unit area. In other words, it is necessary to improve receiving sensitivity. Otherwise, by increasing a transmission sound pressure so as to raise a sound pressure of ultrasonic waves reflected from an object of inspection, the capacitance change at the receiving time can be increased.

In order to improve receiving sensitivity, the spacing between the upper electrode 104 and lower electrode 101 should be narrowed as greatly as possible. Therefore, it is necessary to apply the highest possible dc voltage. However, if an equivalent in vacuum of a magnitude of a deformation of the membrane corresponds to a distance equal to or larger than a one-third of the distance between the electrodes, an electrostatic force between the electrodes gets larger than a spring resilience of the membrane. Eventually, a membrane undersurface 106 comes into contact with a hollow portion bottom 107. The voltage is called a collapse voltage. For these reasons, a dc voltage that is slightly lower than the collapse voltage is applied at the receiving time.

In order to improve a transmission sound pressure, the amplitude of the membrane should preferably be maximized. However, if the membrane undersurface 106 comes into contact with the hollow portion bottom 107, charge injection occurs in the insulating film. This causes a transmitting/receiving characteristic to drift. Therefore, a driving condition for a CMUT has to be designated to such an extent that the membrane undersurface 106 does not come into contact with the hollow portion bottom 107. In reality, since the height of the hollow portion 102 varies due to a fabrication variance, the driving condition is that the membrane should not come into contact with the bottom. In addition, the membrane is designed with a margin preserved, and the amplitude of the membrane is much smaller than the height of the hollow portion 102. Accordingly, the upper limit of the transmission sound pressure is restricted.

Projections of the insulating film jutting out to the hollow portion are formed, and the electrode is pieced in order to realize a structure in which the projections are not sandwiched between the upper and lower electrodes. Thus, the electric field strength at projection contact points is decreased, and charge injection can therefore be avoided. However, since the electrode is pierced, the area of layered portions of the upper and lower electrodes gets smaller. This invites a rise in a driving voltage for a CMUT or degradation in receiving sensitivity.

Figure 4:
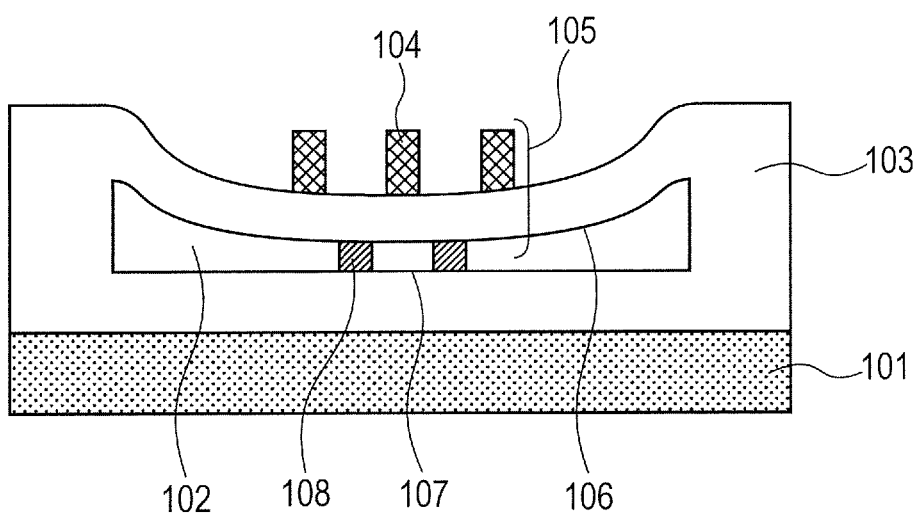
FIG. 4 is a cross-sectional diagram showing a state in which projections of the ultrasonic transducer which the present inventor et al. have discussed come into contact with a hollow portion bottom.
Figure 5:
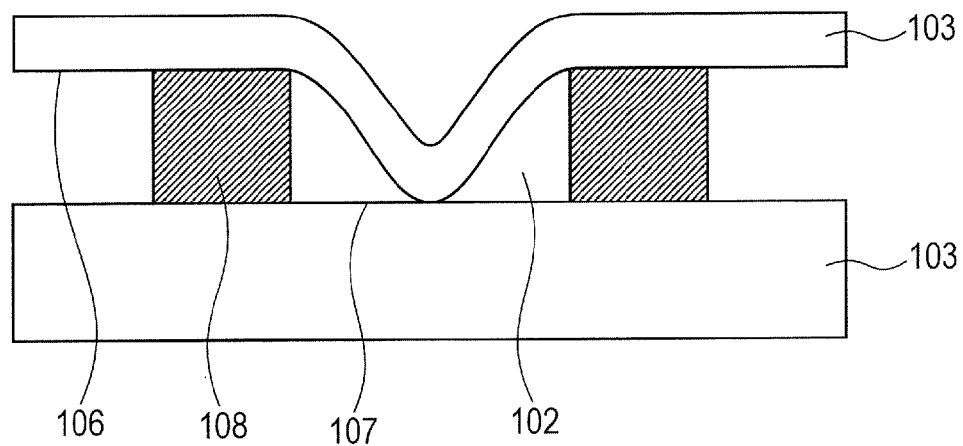
FIG. 5 is a cross-sectional diagram showing a membrane of the ultrasonic transducer, which the present inventor et al. have discussed, that comes into contact with the hollow portion bottom.

In order to realize a high transmission sound pressure without causing a drift in the transmitting/receiving characteristic or inviting a rise in the driving voltage for the CMUT or degradation in receiving sensitivity, it is necessary to minimize the number of projections and an area by which the electrode is pierced. What should be noted will be described below in conjunction with FIG. 4 and FIG. 5. FIG. 4 is a cross-sectional diagram showing a state in which projections 108 formed on the lower side of a membrane 105 are in contact with the hollow portion bottom 107. This state shall be called a projections-in-contact state. In order to obtain the high transmission sound pressure, the amplitude of the membrane should preferably be maximized. Therefore, a voltage equal to or higher than a voltage that brings about the projections-in-contact state is applied. When the voltage equal to or higher than the voltage bringing about the projections-in-contact state is applied, the membrane 105 between the projections 108 deforms to approach the hollow portion bottom 107. The membrane 107 comes into contact with the hollow portion bottom 107 at a voltage equal to or higher than a certain voltage. This state shall be called a membrane-in-contact state, and is shown in FIG. 5. In the membrane-in-contact state, charge injection to the membrane 105 takes place. Therefore, a key to improvement of activity reliability is to expand a voltage margin between the membrane-in-contact state and projections-in-contact state so as to avoid the membrane-in-contact state. In order to expand the voltage margin, the rigidness of the entire membrane should be upgraded. However, since a driving voltage is also raised, it is unacceptable. If the rigidness of the entire membrane observed with the projection undersurfaces 106 in non-contact with the hollow portion bottom 107 is not upgraded but the rigidness of the membrane in the projections-in-contact state is upgraded, the margin voltage can be expanded. The transmission sound pressure can be improved without the drift in the transmitting/receiving characteristic.

The cross-sectional structure of a CMUT in accordance with the present embodiment will be described below in conjunction with FIG. 1. The CMUT includes a parallelepiped lower electrode 201 disposed over a substrate 206, a parallelepiped hollow portion 202 disposed over the lower electrode 201, and a parallelepiped upper electrode 205 disposed over the hollow portion 202. An insulating film 209 is formed to cover the lower electrode 201 between the lower electrode 201 and hollow portion 202, and an insulating film 208 is formed to cover the hollow portion 202 and lower electrode 201 between the upper electrode 205 and hollow portion 202. In the hollow portion 202, at least one or more cylindrical projections 204 that jut out from the undersurface of the insulating film 208 to the hollow portion 202 are disposed. The insulating film 208 is coated with an insulating film 207. The foregoing projections 204 and the insulating films 207, 208, and 209 are made of a silicon oxide or silicon nitride. Over the top of the insulating film 207, at least one or more parallelepiped beam members that are rigid members 203 are disposed. The beam members that are the rigid members 203 may be, similarly to the insulating films 207, 208, and 209, made of the silicon oxide, silicon nitride, or the like, or may be made of another material. A membrane 210 including the insulating film 207, upper electrode 205, and insulating film 208 is vibrated, whereby an ultrasonic wave is transmitted. For convenience' sake, the surfaces of the projections 204 opposed to the insulating film 209 with the hollow portion between them shall be called projection undersurfaces 211, and the surface of the insulating film 209 exposed to the hollow portion shall be called a hollow portion bottom 213. The surface of the membrane 210 exposed to the hollow portion shall be called a membrane undersurface 212. Further, an incident that the projection undersurfaces 211 come into contact with the hollow portion bottom 213 shall be called projection contact, and a voltage at that time shall be called a projection contact voltage. An incident that the membrane undersurface 212 comes into contact with the hollow portion bottom 213 shall be called membrane contact, and a voltage at that time shall be called a membrane contact voltage. A difference between the membrane contact voltage and projection contact voltage shall be called a margin voltage.

A fabrication method for the CMUT shown in FIG. 1 will be described below. The fundamental fabrication method is described in the patent literature 3. Herein, a formation method for a beam member that is the rigid member 203 will be described below. The beam member is formed according to a photography technique and dry etching technique after a thin film which is a material of the beam member, for example, a silicon oxide or silicon nitride is deposited over the insulating film 207 according to a plasma chemical vapor deposition (CVD) method. Since the thickness of the membrane 210 largely affects a device characteristic, dry etching should be carefully performed for fear the insulating film 207 may get thinner. For example, the beam member that is the rigid member 203 is formed as a laminated film having the silicon nitride and silicon oxide layered in that order when viewed from the upper surface, and the insulating film 207 is made of the silicon nitride. Thus, a shaved volume of the insulating film 207, which serves as a bed, to be observed after etching the beam member that is the rigid member 203 is completed gets diminished, and a change in the thickness of the membrane 210 before and after the etching is performed can be suppressed.

The top structure of the CMUT in accordance with the present embodiment will be described in conjunction with FIG. 2. FIG. 2 is the top view of the structure shown in FIG. 1. FIG. 1 is a cross-sectional diagram showing a section cut along a line A-A° in FIG. 2. In FIG. 2, for convenience' sake, the projections 204 or the like are seen through the rigid members 203. Hereinafter, for convenience' sake, as for the hollow portion 202 and upper electrode 205, they shall have a width in the lengthwise direction of the sheet of paper and a lengths thereof in the sideways direction thereof. As for the rigid members 203, they shall have a length in the lengthwise direction of the sheet of paper and a width in the sideways direction thereof. To begin with, the shape of the upper electrode 205 will be described. For example, the upper electrode 205 has plural circular holes. When viewed from the upper surface, the respective projections 204 are disposed nearly in the center positions of the plural circular holes 214 of the upper electrode 205. When viewed from the upper surface, since the projections 204 are disposed in the holes 214 of the upper electrode 205, the projections are located at positions at which the upper electrode 205 is not layered over the projections. In short, the upper electrode 205 is absent from the vertical directions of the projections 204. In FIG. 2, the upper electrode 205 is partly pierced, and is disposed so that the upper electrode 205 is not layered over the projections 204 when viewed from the upper surface. Alternatively, the electrode to be pierced may be the lower electrode 201. What counts is that at least one of the upper electrode 205 and lower electrode 201 should be located at a position at which the electrode is not layered over the projections 204 when viewed from the upper surface. The reason why the disposition is adopted is to increase an inter-electrode distance by piercing the electrode and thus decrease electric field strength for fear a strong electric field may be applied to each of the projections 204 and insulating film 209 and charge injection may thus take place in case a dc voltage or ac voltage is applied across the electrodes and the projection undersurfaces 211 come into contact with the hollow portion bottom 213 accordingly.

The positional relationship between the rigid members 203 and projections 204 will be described in conjunction with FIG. 2. At least one or more projections 204 are disposed in the center in the width direction of the hollow portion 202 when viewed from the upper surface. The rigid members 203 are disposed so that they are even partly layered over the holes 214 of the upper electrode 205 and the projections 204 alike when viewed from the upper surface. In FIG. 1 and FIG. 2, the rigid members 203 and projections 204 are equidistantly disposed in the length direction of the hollow portion when viewed from the upper surface. Alternatively, the rigid members 203 and projections 204 may be disposed non-equidistantly. However, in this case, plural membrane contact voltages are present within one CMUT. This is not preferred in terms of design. Therefore, the rigid members and projections should be disposed equidistantly. The spacing between the rigid members 203 or between the projections 204 should be determined based on the magnitude relationship between the membrane contact voltage and projection contact voltage. For example, if the membrane contact voltage is lower than the projection contact voltage, the spacing between the rigid members 203 or projections 204 is narrowed in order to raise the membrane contact voltage. However, when the spacing between the projections 204 is narrowed, the area of the upper electrode 205 decreases. This invites degradation in sensitivity of the CMUT. Therefore, an inter-projection spacing that meets a margin voltage which is minimum necessary on a design stage should be adopted.

Figure 1:
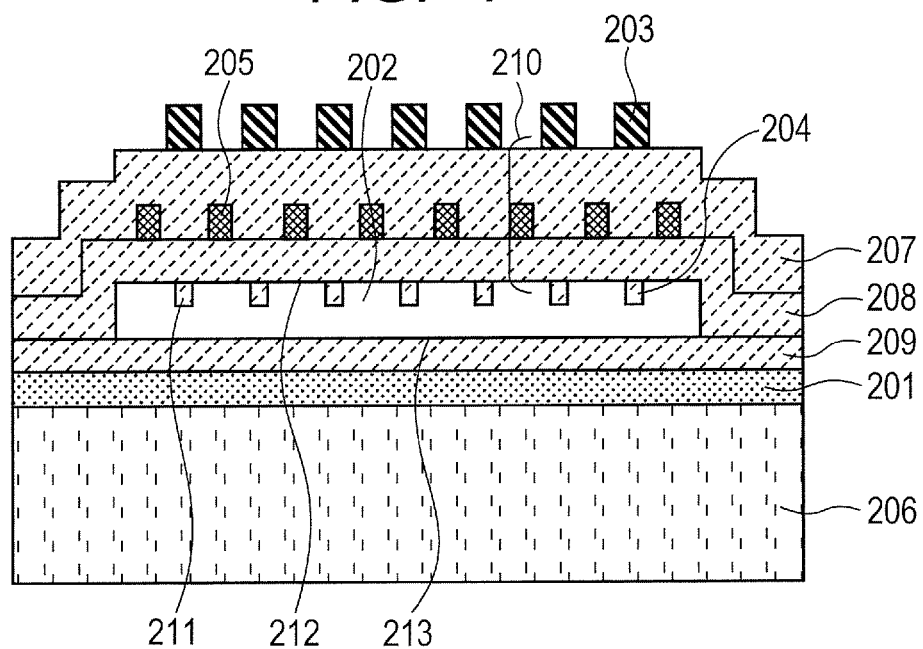
FIG. 1 is a cross-sectional diagram of an ultrasonic transducer in accordance with an embodiment 1 of the present invention.
Figure 2:
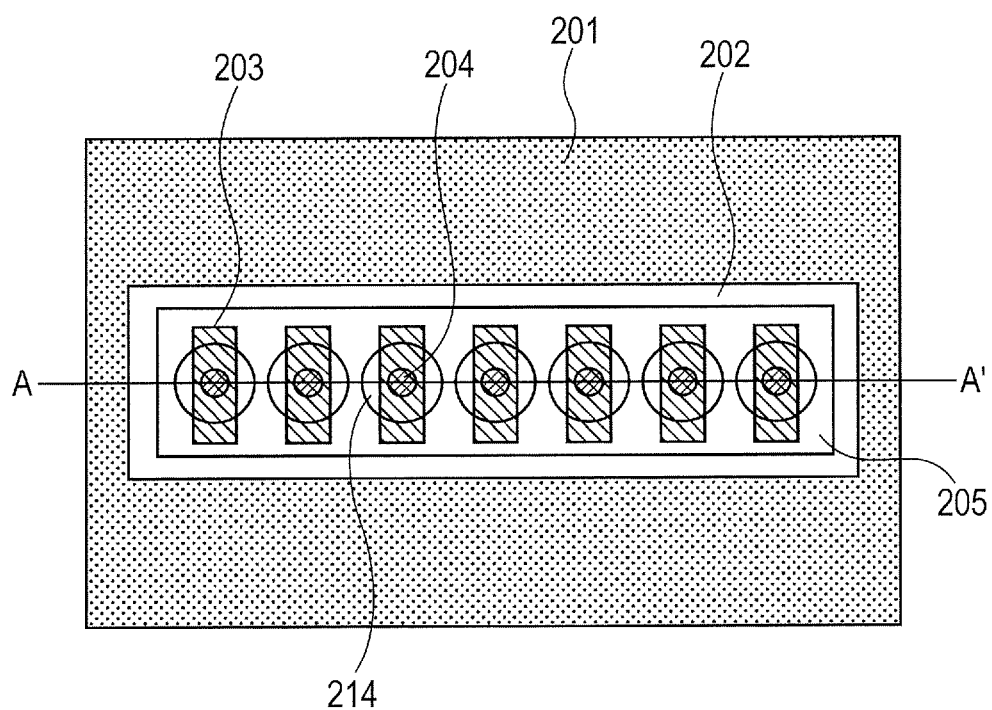
FIG. 2 is a top view of the ultrasonic transducer in accordance with the embodiment 1 of the present invention.

A feature of the embodiment 1 is, as shown in FIG. 1 and FIG. 2, that the CMUT has at least one of the upper electrode 205 and lower electrode 201 located at a position at which the electrode is not layered over the projections 204, which jut out to the hollow portion 202, when viewed from the upper surface. In the CMUT, the rigid members 203 included in the membrane 210 and the projections 204 are disposed to be even partly layered when viewed from the upper surface. Owing to the structure, the membrane immediately above the projections 204 gets thicker, rigidness is upgraded, and a margin voltage can be raised. In other words, even when the membrane 210 is vibrated to the greatest extent for the purpose of obtaining a high transmission sound pressure under a driving condition that the projection undersurfaces 211 come into contact with the hollow portion bottom 213, membrane contact can be prevented. In an actual CMUT, the membrane contact voltage may be partly lower than a design value because of a fabrication variance. By adopting the foregoing structure, the membrane contact can be prevented, and charge injection to the insulating film 208 of the membrane 210 can be minimized. Eventually, the activity reliability of the CMUT can be improved.

Figure 6:
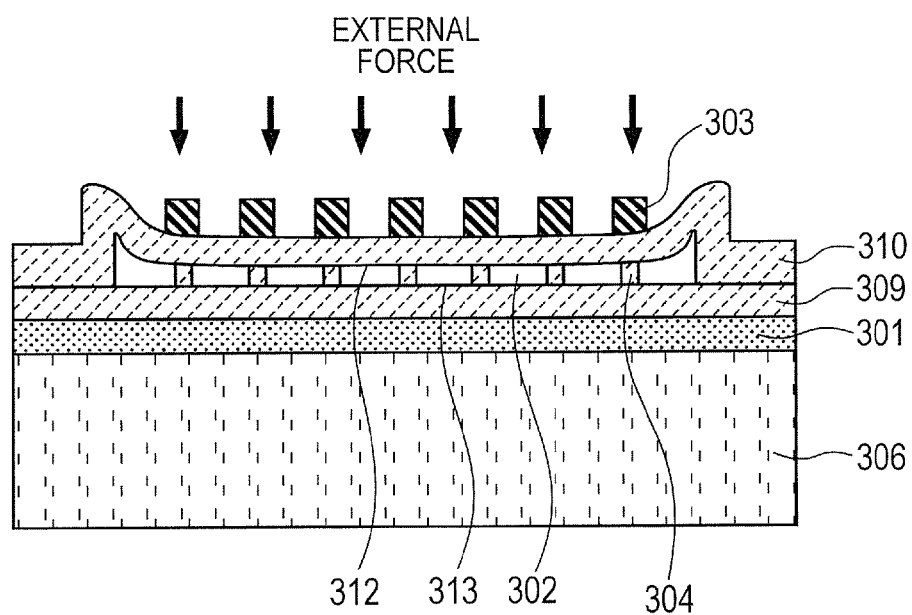
FIG. 6 is a cross-sectional diagram showing a state in which the projections come into contact with the hollow portion bottom.
Figure 7:
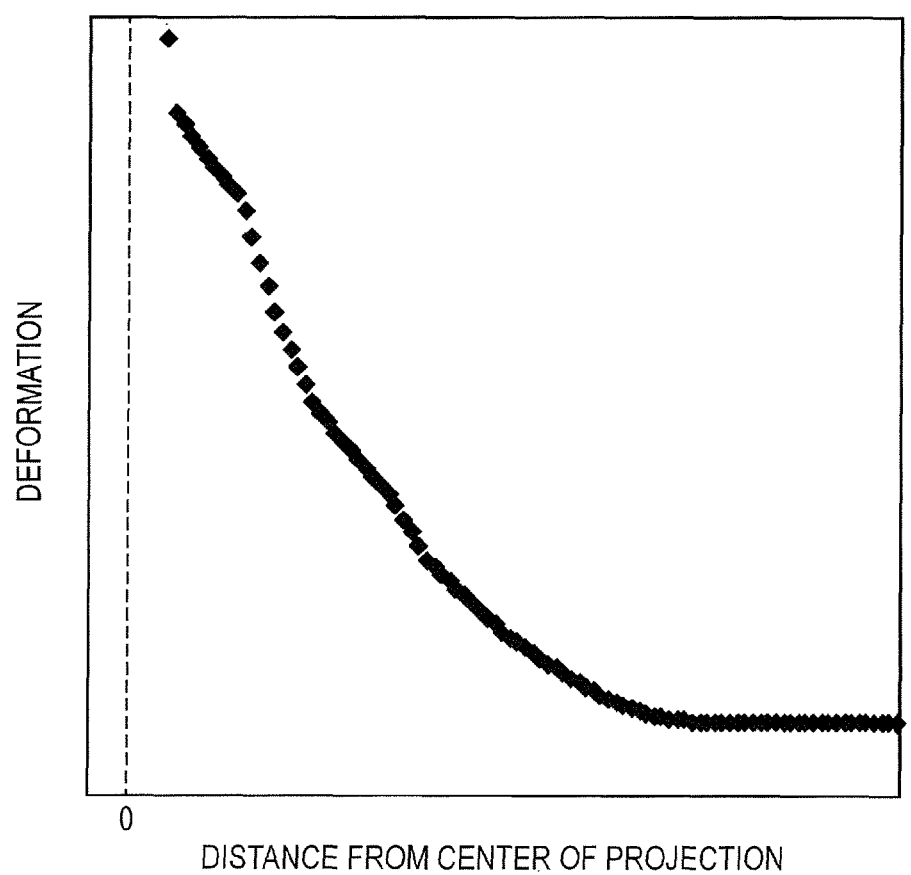
FIG. 7 is a graph plotted based on a distance from the center of a projection in order to express a deformation of the membrane occurring when a certain external force is applied to the membrane with the projections brought into contact with the hollow portion bottom.
Figure 8A:
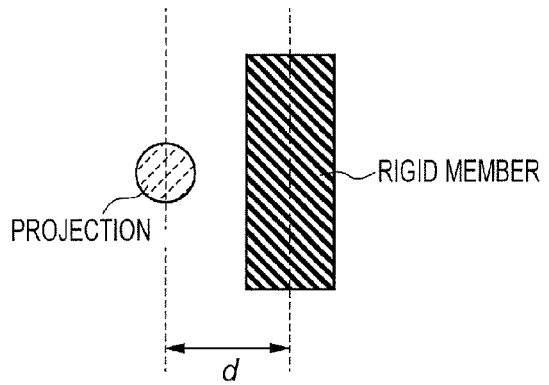
FIG. 8A shows the positional relationship between a rigid member and a projection.
Figure 8B:
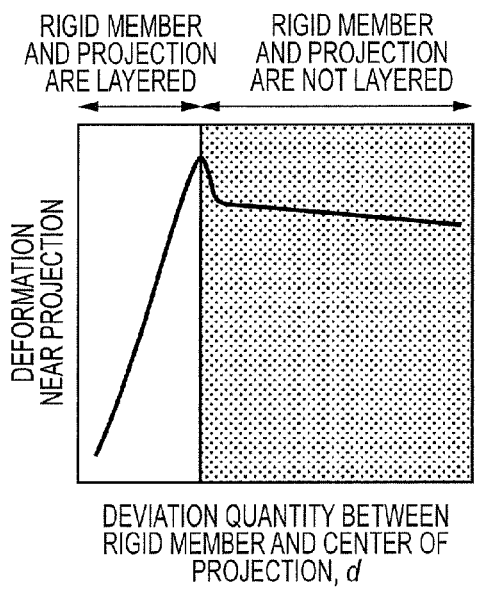
FIG. 8B is a graph expressing a relationship between a deviation quantity of a rigid member disposed in the membrane from the center of a projection and a deformation near the projection.
Figure 8C:
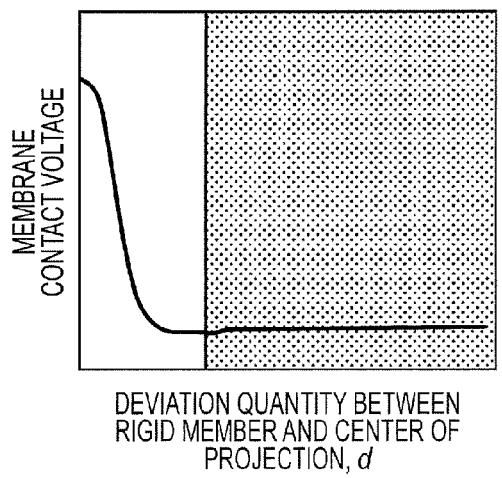
FIG. 8C is a graph expressing a relationship between a deviation quantity of a rigid member disposed in the membrane from the center of a projection and a membrane contact voltage.
Figure 9:
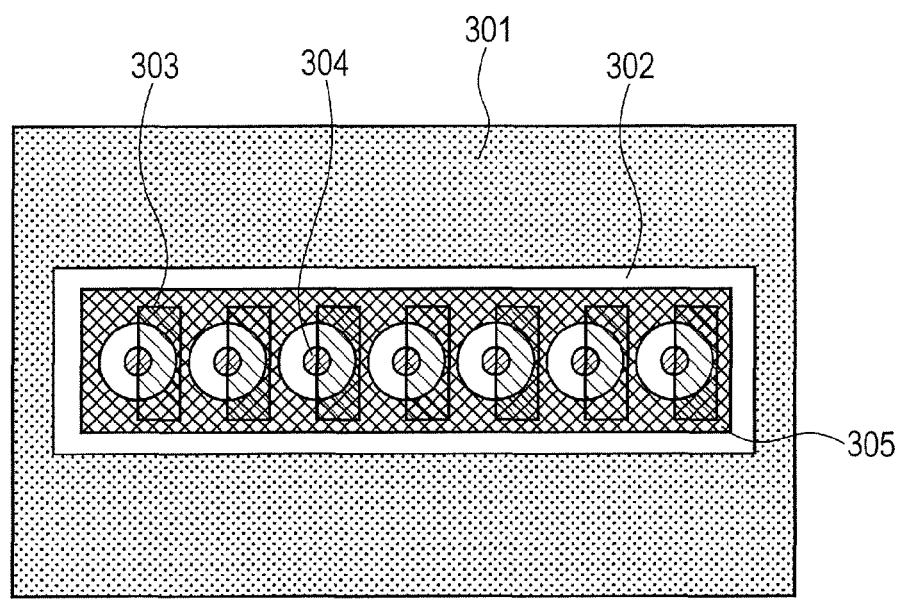
FIG. 9 is a top view of the ultrasonic transducer in accordance with the embodiment 1 of the present invention showing a case where the centers of the rigid members do not coincide with the centers of the projections.
Figure 10:
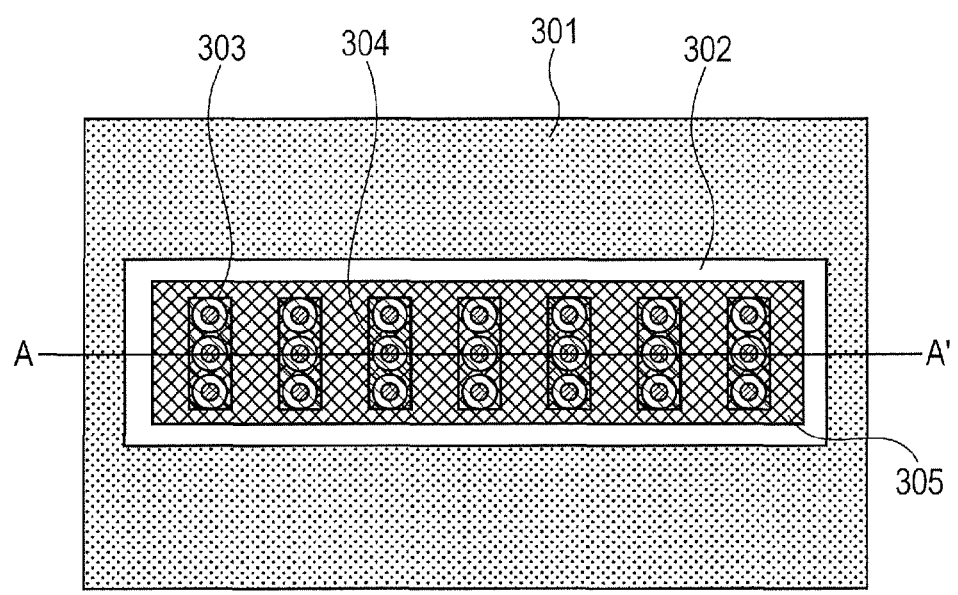
FIG. 10 is a top view of the ultrasonic transducer in accordance with the embodiment 1 of the present invention showing a case where one of the rigid members is layered over plural projections.
Figure 11:
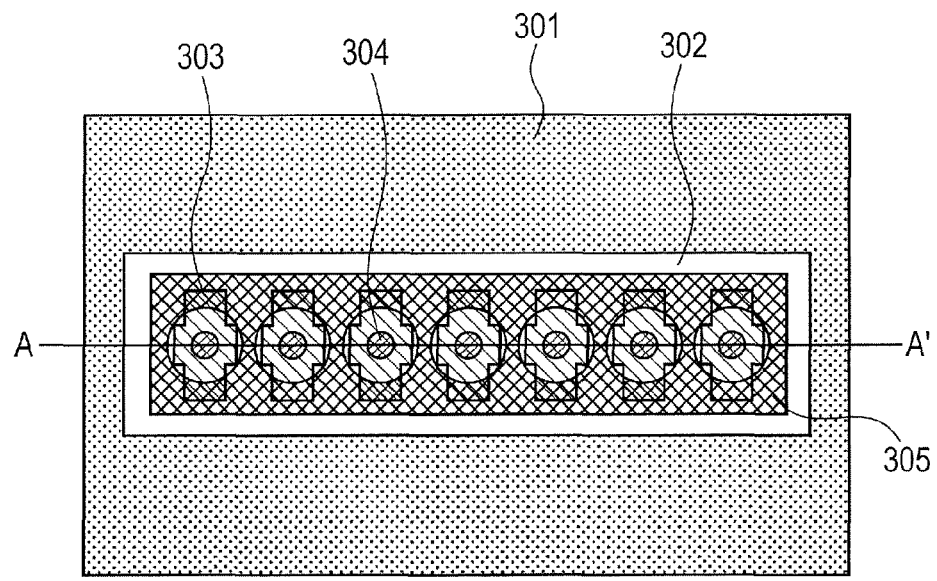
FIG. 11 is a top view of the ultrasonic transducer in accordance with the embodiment 1 of the present invention showing a case where the rigid members are cruciform.
Figure 12:
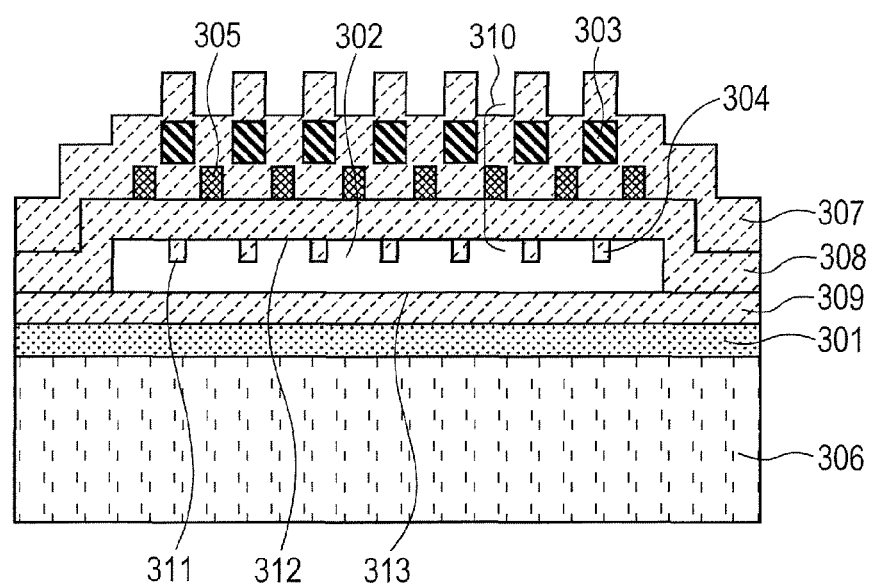
FIG. 12 is a cross-sectional diagram of another ultrasonic transducer in accordance with the embodiment 1 of the present invention.

The reason why disposing the rigid member 203 and projection 204 so that the rigid members 203 and projections 204 are even partly layered when viewed from the upper surface is advantageous will be described in conjunction with FIG. 6. Noted herein is a point that the membrane 210 in the fields in which the membrane 210 is layered over the projections 204 when viewed from the upper surface is made thicker in order to locally upgrade rigidness. In FIG. 6, the insulating film 207, upper electrode 205, and insulating film 208 shown in FIG. 1 are all shown as a membrane 310. FIG. 7 shows a result of simulation obtained by uniformly applying an external force of a certain magnitude to the entire membrane 310 in a projections-in-contact state shown in FIG. 6, and plotting the deformation of the membrane 310 in relation to a distance from the center of the projection 304. The deformation takes on a maximum value near the projection 304, and monotonously decreases as the projection gets farther. The result signifies that when the membrane 310 deforms in the projections-in-contact state, since the projection 304 serves as a fixed end, the deformation near the projection 304 is maximized. Therefore, if the deformation near the projection can be minimized, a margin voltage can be expanded. FIG. 8A to FIG. 8C include graphs expressing the relationship between the positional relationship between a rigid member and a projection and the magnitude of the deformation near the projection. As shown in FIG. 8B, when a deviation quantity d between the rigid member and projection is small, the deformation near the projection is small. When the center of the rigid member coincides with the center of the projection, the deformation is a minimum. In contrast, when the rigid member and projection are not layered, the deformation near the projection is large. FIG. 8C shows the relationship between the deviation quantity d between the rigid member and projection and a membrane contact voltage. When the deviation quantity d is small, the membrane contact voltage is high. When the deviation quantity d gets larger, the membrane contact voltage decreases. Accordingly, wherever the rigid member is disposed largely affects the deformation near the projection. When the rigid member is disposed so that the center of the rigid member coincides with the center of the projection, the deformation near the projection is minimized. The deposition is therefore effective. However, similarly to a structure shown in FIG. 9 that is a top view, when parallelepiped rigid members 303 and cylindrical projections 304 are even partly layered when viewed from the upper surface, an effect of minimizing the deformations near the respective projections is exerted. The shape and disposition of the rigid members 303 viewed from the upper surface should be appropriately determined depending on a desired frequency characteristic. As shown in FIG. 10, one parallelepiped rigid member 303 may be layered over at least parts of plural cylindrical projections 304 when viewed from the upper surface. Even in this structure, the plural projections 304 are disposed so that the upper electrode 305 is not layered over the plural projections 304. The rigid members 303 are disposed to be at least partly layered over the plural projections 304 when viewed from the upper surface. The structure would prove useful as a means for raising the membrane contact voltage in case the width of a hollow portion 302 is large and the rigidness in the width direction of the hollow portion is low. However, when the number of projections 304 is increased, the area of the upper electrodes 305 is decreased and the sensitivity of the CMUT is degraded. The number of projections 304 should be a minimum necessary value. As shown in FIG. 11, the shape of the rigid members 303 may be cruciform. In this structure, at a position in a membrane between the projections 304 at which the rigid member 303 is located, the membrane gets thicker. Thus, the rigidness can be improved, and the contact voltage of the inter-projection membrane can be raised. By enlarging the width of the rectangular rigid members 203 shown in FIG. 2, the rigidness of the inter-projection membrane can be upgraded. However, the area of the rigid members 203 gets larger, the rigidness of the entire membrane gets higher, and a driving voltage gets higher. This is disadvantageous in terms of reliability. Namely, the cruciform rigid members 303 shown in FIG. 11 make it possible to raise the contact voltage of the inter-projection membrane without a large change in the driving voltage. The structures having rigid members disposed over the surface of the membrane have been described so far. Alternatively, as shown in FIG. 12, the rigid members 303 may be embedded in the membrane 310. The shape of the membrane 310 is preferably flat, but may dilate or dent due to residual stresses of films included. As shown in FIG. 12, by varying the positions at which the respective rigid members 303 are embedded, a residual stress distribution in the membrane 310 can be controlled. The dilated or dented shape of the membrane 310 can be controlled.

Embodiment 2

Figure 13:
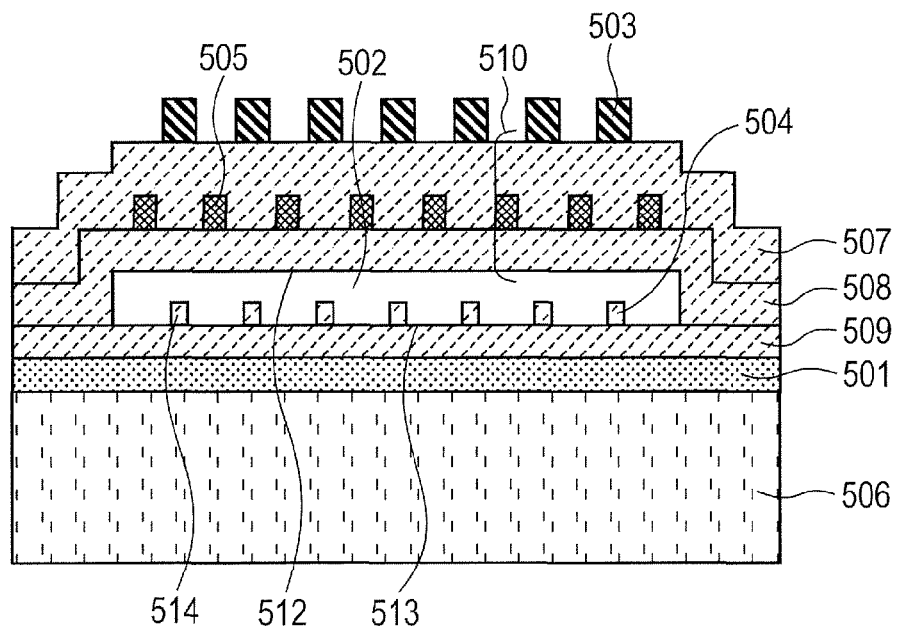
FIG. 13 is a cross-sectional diagram of an ultrasonic transducer in accordance with an embodiment 2 of the present invention.

The structure of a CMUT in accordance with an embodiment 2 will be described in conjunction with FIG. 13. The CMUT includes a parallelepiped lower electrode 501 disposed over a substrate 506, a hollow portion 502 disposed over the lower electrode 501, and a parallelepiped upper electrode 505 disposed over the hollow portion 502. An insulating film 509 is formed to cover the lower electrode 501 between the lower electrode 501 and hollow portion 502, and an insulating film 508 is formed to cover the hollow portion 502 and lower electrode 501 between the upper electrode 505 and hollow portion 502. At least one or more cylindrical projections 504 jutting out from the top of the insulating film 509 to the hollow portion 502 are disposed in the hollow portion 502. The projections 504 are formed with the insulating film. Over the top of the insulating film 507, at least one or more parallelepiped rigid members 503 are disposed. Beam members that are the rigid members 503 may be, similarly to the insulating films 507, 508, and 509, made of a material such as a silicon oxide or silicon nitride, or may be made of another material. A membrane 510 including the insulating film 507, upper electrode 505, and insulating film 508 is vibrated in order to transmit an ultrasonic wave. Hereinafter, for convenience' sake, the surfaces of the projections 504 opposed to the insulating film 508 with the hollow portion between them shall be called projection tops 514, and the surface of the insulating film 509 exposed to the hollow portion shall be called a hollow portion bottom 513. The surface of the membrane 510 exposed to the hollow portion shall be called a membrane undersurface 512. An incident that the projection tops 514 come into contact with the membrane undersurface 512 shall be called projection contact, and a voltage at that time shall be called a projection contact voltage. An incident that the membrane undersurface 512 comes into contact with the hollow portion bottom 513 shall be called membrane contact, and a voltage at that time shall be called a membrane contact voltage. A difference between the membrane contact voltage and projection contact voltage shall be called a margin voltage. The spacing between the rigid members 503 or projections 504 should be, similarly to the contents described in relation to the embodiment 1, determined based on the magnitude relationship between the membrane contact voltage and projection contact voltage. For example, when the membrane contact voltage is lower than the projection contact voltage, the spacing between the rigid members 503 or between the projections 504 is narrowed in order to raise the membrane contact voltage.

A difference from the aforesaid embodiment 1 lies in a point that the projections 504 jut out from the hollow portion bottom 513 to the hollow portion 502. In this structure, if the membrane undersurface 512 comes into contact with the projection tops 514, the structure becomes identical to the structure that is shown in FIG. 6 and that has the projections 304 jutted out from the membrane undersurface 312 to the hollow portion 302. Even in the structure having the projections 504 jutted out from the hollow portion bottom 513, if the centers of the rigid members coincide with the centers of the projections when viewed from the upper surface, the difference between a projection contact voltage and membrane contact voltage can be increased. Therefore, the same advantage as that of the ultrasonic transducer of the embodiment 1 can be provided.

Figure 14:
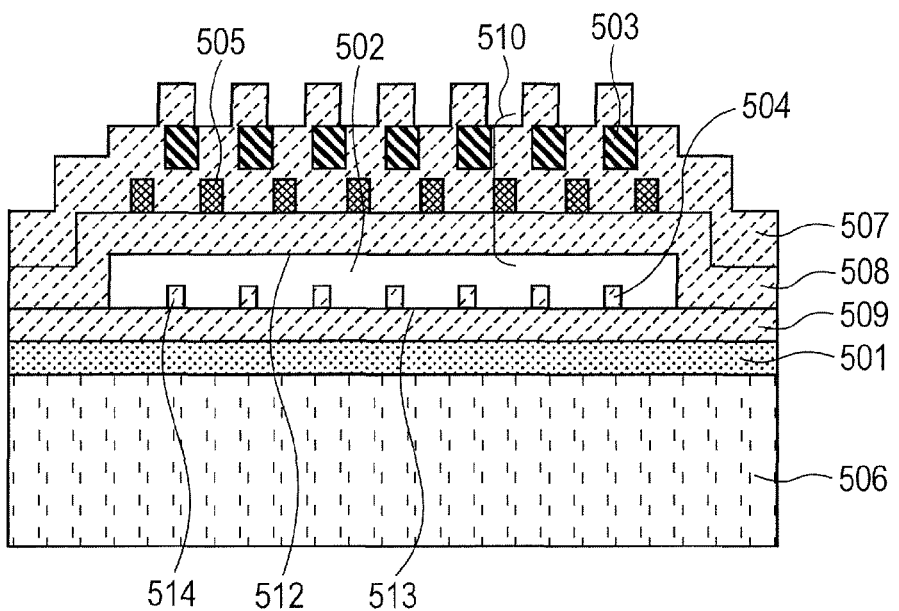
FIG. 14 is a cross-sectional diagram of another ultrasonic transducer in accordance with the embodiment 2 of the present invention.

Similarly to the ultrasonic transducer of the embodiment 1, the disposition in which the centers of the rigid members 503 coincide with the centers of the projections 504 when viewed from the upper surface provides the greatest advantage. If the rigid members are even partly layered over the projections, an advantage is provided. When this structure is adopted, since the projections are absent from the membrane side of a CMUT vibration unit, the frequency characteristic of the CMUT can be readily designed. The structure having the rigid members disposed over the surface of the membrane has been described so far. Alternatively, as shown in FIG. 14, the rigid members 503 may be embedded in the membrane 510. This is advantageous as mentioned in relation to the embodiment 1 in that the shape of the membrane 510 can be readily controlled.

Embodiment 3

Figure 15:
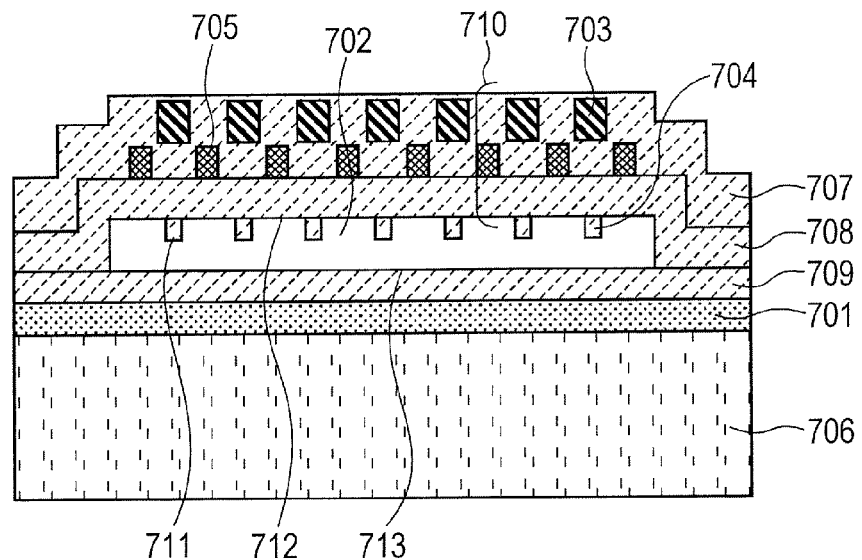
FIG. 15 is a cross-sectional diagram of an ultrasonic transducer in accordance with an embodiment 3 of the present invention.

The structure of a CMUT in accordance with an embodiment 3 will be described in conjunction with FIG. 15 and FIG. 16. FIG. 15 is a cross-sectional diagram showing one CMUT. A CMUT cell includes a parallelepiped lower electrode 701, a hollow portion 702 disposed over the lower electrode 701, a parallelepiped upper electrode 705 disposed over the hollow portion 702, or the like. An insulating film 709 is formed to cover the lower electrode 701 between the lower electrode 701 and hollow portion 702, and an insulating film 708 is formed to cover the hollow portion 702 and lower electrode 701 between the upper electrode 705 and hollow portion 702. At least one or more cylindrical projections 704 that jut out from the undersurface of the insulating film 708 to the hollow portion 702 are disposed in the hollow portion 702. The projections 704 are formed with the insulating film. The projections 704 and insulating films 707, 708, and 709 are made of a silicon oxide, silicon nitride, or the like. Parallelepiped high-Young's modulus members 703 are embedded in a membrane 710. In FIG. 15, the high-Young's modulus members 703 are embedded in the insulating film 707. Alternatively, the high-Young's modulus members 703 may be embedded in the insulating film 708, or may be embedded in both of the insulating film 707 and insulating film 708. The high-Young's modulus members 703 are made of a material whose Young's modulus is higher than that of the surrounding insulating film 707 or insulating film 708, for example, a metallic material such as tungsten or a ceramic material such as alumina, or formed by reforming the insulating film 707 or insulating film 708 through ion implantation so as to improve the Young's modulus. Hereinafter, for convenience' sake, the surfaces of the projections 704 opposed to the insulating film 709 with the hollow portion between them shall be called projection undersurfaces 711, and the surface of the insulating film 709 exposed to the hollow portion shall be called a hollow portion bottom 713. The surface of the membrane 710 exposed to the hollow portion shall be called a membrane undersurface 712. An incident that the projection undersurfaces 711 come into contact with the hollow portion bottom 713 shall be called projection contact, and a voltage at that time shall be called a projection contact voltage. An incident that the membrane undersurface 712 comes into contact with the hollow portion bottom 713 shall be called membrane contact, and a voltage at that time shall be called a membrane contact voltage.

The positional relationship between the high-Young's modulus members 703 and projections 704 will be described below in conjunction with FIG. 16. FIG. 15 is a cross-sectional diagram showing a section cut along a line A-A' in FIG. 16. In FIG. 16, for convenience' sake, the projections 704 and others are seen through the high-Young's modulus members 703. Hereinafter, for convenience' sake, as for the hollow portion 702 and upper electrode 705, they shall have a width in the lengthwise direction of a sheet of paper and a length in the sideways direction thereof. As for the high-Young's modulus members 703, they shall have a length in the lengthwise direction of the sheet of paper and a width in the sideways direction thereof. At least one or more projections 704 are disposed in the center in the width direction of the hollow portion 702 when viewed from the upper surface. The high-Young's modulus members 703 are disposed so that the centers thereof coincide with the centers of the projections 704 when viewed from the upper surface. At least one of the upper electrode 705 and lower electrode 701 is located at a position at which the electrode is not layered over the projections 704 when viewed from the upper surface. In FIG. 16, the upper electrode 705 is partly pierced and disposed so that the projections 704 and upper electrode 705 are not layered when viewed from the upper surface. Alternatively, the electrode to be pierced may be the lower electrode 701. The reason why the disposition is adopted is to increase an inter-electrode distance by piercing the electrode and thus decrease electric field strength for fear a strong electric field may be applied to each of the projections 704 and insulating film 709 and charge injection may thus take place in case a dc voltage or ac voltage is applied across the electrodes and the projection undersurfaces 711 come into contact with the hollow portion bottom 713 accordingly. In FIG. 15 and FIG. 16, the high-Young's modulus members 703 and projections 704 are equidistantly disposed in the length direction of the hollow portion. Alternatively, the high-Young's modulus members 703 and projections 704 may be non-equidistantly disposed. However, when the high-Young's modulus members 703 and projections 704 are non-equidistantly disposed, plural membrane contact voltages are present in one CMUT. This is not preferred in terms of design. Therefore, the high-Young's modulus members 703 and projections 704 should be equidistantly disposed. The spacing between the high-Young's modulus members 703 or between the projections 704 may be determined based on the magnitude relationship between the membrane contact voltage and projection contact voltage. For example, if the membrane contact voltage is lower than the projection contact voltage, the spacing between the high-Young's modulus members 703 or between the projections 704 is narrowed in order to improve the membrane contact voltage.

Figure 16:
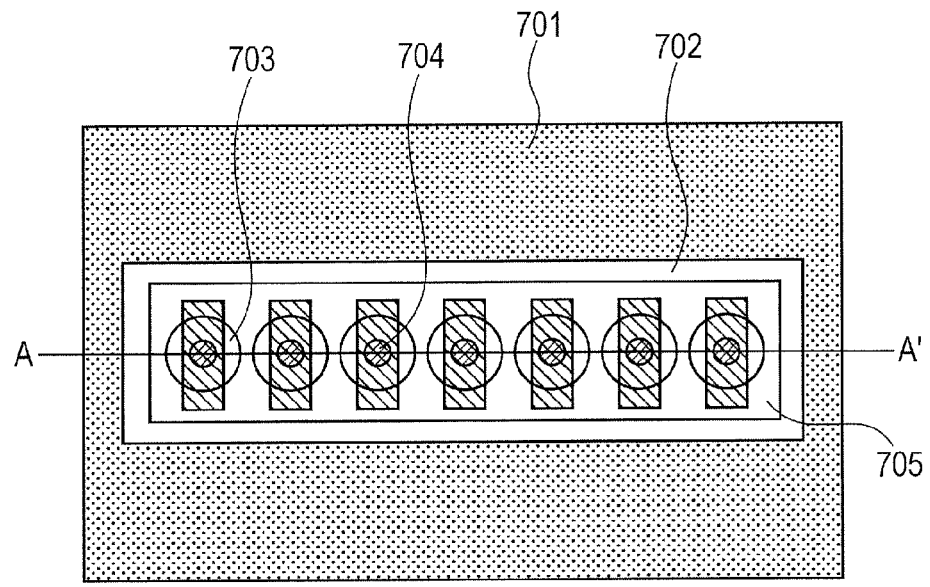
FIG. 16 is a top view of the ultrasonic transducer in accordance with the embodiment 3 of the present invention.

The feature of the embodiment 3 is, as shown in FIG. 15 and FIG. 16, that in the CMUT having at least one of the upper electrode 705 and lower electrode 701 disposed at a position at which the electrode is not layered over the projections 704, which jut out to the hollow portion 702, when viewed from the upper surface, the high-Young's modulus members 703 included in the membrane 710 and the projections 704 are disposed to be even partly layered when viewed from the upper surface. Noted herein is a point that the high-Young's modulus members are disposed within the membrane in fields, in which the membrane is layered over the projections 704 when viewed from the upper surface, in order to locally upgrade rigidness. Owing to the structure, the difference between the projection contact voltage and membrane contact voltage can be made larger. In other words, even when the membrane 710 is vibrated to the greatest extent in order to obtain a high transmission sound pressure under a driving condition that the projection undersurfaces 711 come into contact with the hollow portion bottom 713, membrane contact can be prevented. In an actual CMUT, the membrane contact voltage may be partly lower than a design value because of a variance stemming from fabrication. When the foregoing structure is adopted, the membrane contact can be prevented, and charge injection into the insulating film 708 of the membrane 710 can be minimized. Therefore, the activity reliability of the CMUT can be improved. In addition, the CMUT surface can be evened.

Embodiment 4

Figure 17:
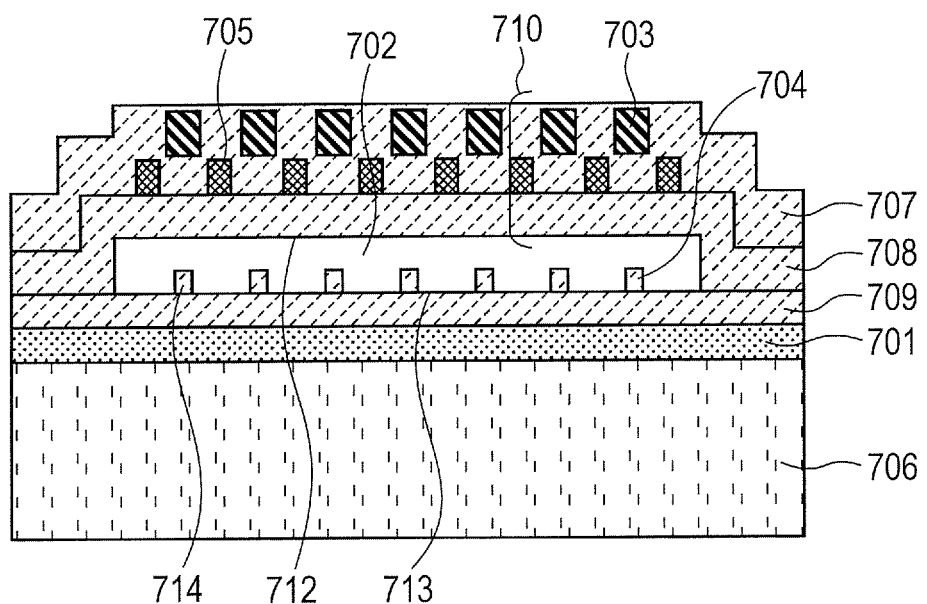
FIG. 17 is a cross-sectional diagram of an ultrasonic transducer in accordance with an embodiment 4 of the present invention.

The structure of a CMUT in accordance with an embodiment 4 will be described in conjunction with FIG. 17. The CMUT includes a parallelepiped lower electrode 701 disposed over a substrate 706, a hollow portion 702 disposed over the lower electrode 701, and a parallelepiped upper electrode 705 disposed over the hollow portion 702. An insulating film 709 is formed to cover the lower electrode 701 between the lower electrode 701 and hollow portion 702, and an insulating film 708 is formed to cover the hollow portion 702 and lower electrode 701 between the upper electrode 705 and hollow portion 702. At least one or more cylindrical projections 704 jutting out from the top of the insulating film 709 to the hollow portion 702 are disposed in the hollow portion 702. The projections 704 are formed with the insulating film. Over the top of the insulating film 707, at least one or more parallelepiped high-Young's modulus members 703 are embedded. For convenience' sake, the surfaces of the projections 704 opposed to the insulating film 708 with the hollow portion between them shall be called projection tops 714, and the surface of the insulating film 709 exposed to the hollow portion shall be called a hollow portion bottom 713. The surface of a membrane 710 exposed to the hollow portion shall be called a membrane undersurface 712. An incident that the projection tops 714 come into contact with the membrane undersurface 712 shall be called a projection contact, and a voltage at that time shall be called a projection contact voltage. An incident that the membrane undersurface 712 comes into contact with the hollow portion bottom 713 shall be called a membrane contact, and a voltage at that time shall be called a membrane contact voltage. The spacing between the high-Young's modulus members 703 or projections 704 should be determined based on the magnitude relationship between the membrane contact voltage and projection contact voltage. For example, when the membrane contact voltage is lower than the projection contact voltage, the spacing between the high-Young's modulus members 703 or between the projections 704 is narrowed in order to raise the membrane contact voltage.

A difference from the aforesaid embodiment 3 lies in a point that the projections 704 jut out from the hollow portion bottom 713 to the hollow portion 702. In this structure, if the membrane undersurface 712 comes into contact with the projection tops 714, the same state as the projections-in-contact state of the structure shown in FIG. 15 is attained. Therefore, even in the structure having the projections 704 jutted out from the hollow portion bottom 713, if the centers of the high-Young's modulus members coincide with the centers of the projections when viewed from the upper surface, the difference between the projection contact voltage and membrane contact voltage can be made larger, and the activity reliability of the CMUT can be improved. Therefore, the same advantage as that of the ultrasonic transducer of the embodiment 3 can be provided. Similarly to the ultrasonic transducer of the embodiment 3, if the high-Young's modulus members and projections are even partly layered when viewed from the upper surface, an advantage is provided. When the structure is adopted, since the projections are absent from the membrane side of the CMUT vibration unit, the frequency characteristic of the CMUT can be readily designed.

Embodiment 5

Figure 18:
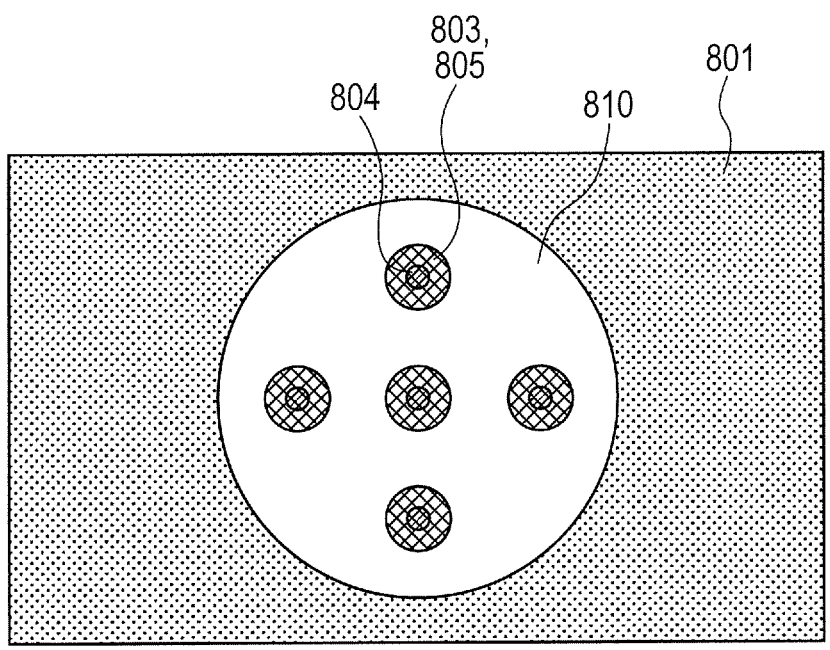
FIG. 18 is a top view of an ultrasonic transducer in accordance with an embodiment 5 of the present invention.

FIG. 18 is a top view showing an ultrasonic transducer of an embodiment 5. The ultrasonic transducer includes circular projections 804, a circular membrane 810, and circular rigid members 803 or high-Young's modulus members 805 disposed over the top of the membrane 810. The rigid members 803 and projections 804 are disposed in the center of the membrane 801 and at intermediate positions between the center of the membrane and each of the upper, lower, left, and right membrane edges. The rigid members 803 and projections 804 are disposed so that they are partly layered when viewed from the upper surface. The circular projections 804 are an example. A triangular, pentagonal, heptagonal, or any other polygonal shape will do. Even for the rigid members 803 or high-Young's modulus members 805, the circular shape is an example, but a triangular, pentagonal, heptagonal, or any other polygonal shape will do. The number of rigid members 803 or projections 804, and the disposition thereof may be determined based on the magnitude relationship between a projection contact voltage and a membrane contact voltage. For example, if the membrane contact voltage is lower than the projection contact voltage in the structure shown in FIG. 18, the number of rigid members 803 or projections 804 should be increased. In that case, the dispositional positions should be points at which the membrane comes into contact with the projections with the membrane contact voltage.

Embodiment 6

Figure 19:
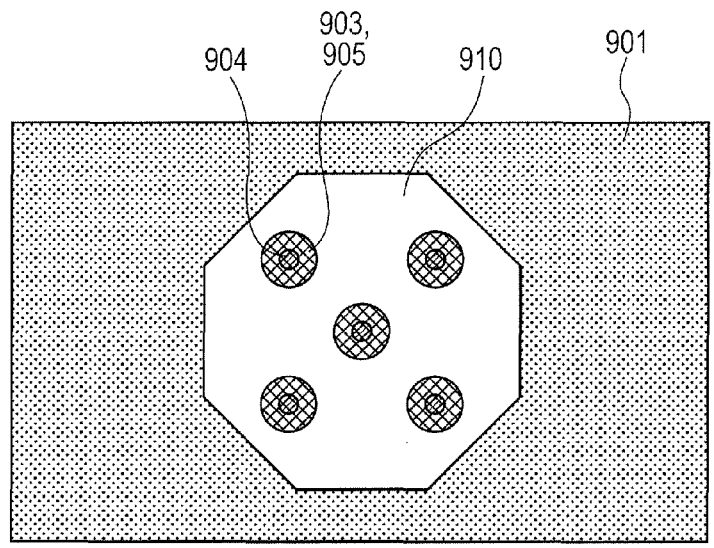
FIG. 19 is a top view of an ultrasonic transducer in accordance with an embodiment 6 of the present invention.

FIG. 19 is a top view showing an ultrasonic transducer of an embodiment 6. The ultrasonic transducer includes circular projections 904, an octagonal membrane 910, and circular rigid members 903 or high-Young's modulus members 905 disposed over the top of the membrane 910. The rigid members 903 and projections 904 are disposed in the center of the membrane 910 and around the center thereof. The rigid members 903 and projections 904 are disposed so that they are partly layered when viewed from the upper surface. The octagonal membrane 901 is an example. A triangular, pentagonal, heptagonal, or any other polygonal shape will do. The circular projections 904 are an example. A triangular, pentagonal, heptagonal, or any other polygonal shape will do. Even for the rigid members 903 or high-Young's modulus members 905, the circular shape is an example, but a triangular, pentagonal, heptagonal, or any other polygonal shape will do. The number of rigid members 903 or projections 904 and the disposition thereof may be determined based on the magnitude relationship between a projection contact voltage and membrane contact voltage. For example, if the membrane contact voltage is lower than the projection contact voltage in the structure shown in FIG. 19, the number of rigid members 903 or projections 904 should be increased. In that case, the dispositional positions should be points at which the membrane comes into contact with the projections with the membrane contact voltage.

Embodiment 7

Figure 20:
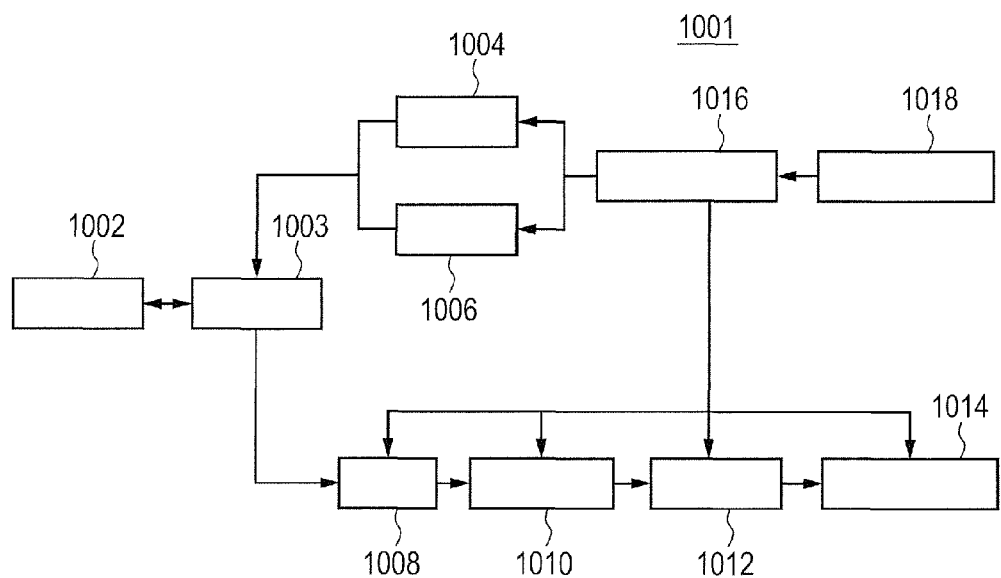
FIG. 20 is a block diagram of the configuration of an ultrasonic diagnostic equipment in accordance with an embodiment 7 of the present invention.

Referring to FIG. 20, the configuration of an ultrasonic diagnostic equipment including an ultrasonic transducer of the present invention, and the activities thereof will be described below. An ultrasonic diagnostic equipment 1001 includes an ultrasonic probe 1002, a transmitting/receiving separation unit 1003, a transmission unit 1004, a bias unit 1006, a receiving unit 1008, a phasing and summation unit 1010, an image processing unit 1012, a display unit 1014, a control unit 1016, and an operation unit 1018.

The ultrasonic probe 1002 is a device that is brought into contact with a subject and transmits or receives ultrasonic waves to or from the subject. The ultrasonic waves are transmitted from the ultrasonic probe 1002 to the subject, and reflected echo signals sent from the subject are received by the ultrasonic probe 1002. The ultrasonic transducer in accordance with any of the embodiments 1 to 6 is stored in the ultrasonic probe 1002, and electrically coupled to the transmitting/receiving separation unit 1003 to be described later. The transmission unit 1004 and bias unit 1006 are devices that feed a driving signal to the ultrasonic probe 1002. The receiving unit 1008 is a device that receives the reflected echo signals outputted from the ultrasonic probe 1002. The receiving unit 1008 further performs such processing as analog-to-digital conversion on the received reflected echo signals. The transmitting/receiving separation unit 1003 switches or separates transmitting and receiving, so that the driving signal can be passed from the transmission unit 1004 to the ultrasonic probe 1002 during transmission, or a receiving signal can be passed from the ultrasonic probe 1002 to the receiving unit 1008 during receiving. The phasing and summation unit 1010 is a device that phases and summates received reflected echo signals. The image processing unit 1010 is a device that constructs a diagnostic image (for example, a tomographic image or bloodstream image) on the basis of the phased and summated reflected echo signals. The display unit 1014 is a display device that displays the diagnostic image which has undergone image processing. The control unit 1016 is a device that controls the foregoing components. The operation unit 1018 is a device to be used to give instructions to the control unit 1016. The operation unit 1018 includes pieces of input equipment, for example, a trackball, a keyboard, and a mouse.

INDUSTRIAL APPLICABILITY

The ultrasonic transducer of the present invention can be employed in an ultrasonic diagnostic equipment including an ultrasonic probe, a defect inspection apparatus for the interior of a structure, an object position sensing apparatus, a flow velocity measurement apparatus, or the like. A high transmission sound pressure and high receiving sensitivity can be realized. In addition, reliability in long-term driving can be improved.

REFERENCE SINGS LIST 201, 301, 501, 701, 801, 901: lower electrode
202, 302, 502, 702: hollow portion
207, 208, 209, 309, 507, 508, 509, 707, 708, 709: insulating film
205, 305, 505, 705: upper electrode
210, 310, 510, 710, 810, 910: membrane
213, 313, 513, 713: hollow portion bottom
203, 303, 503, 803, 903: rigid member
204, 304, 504, 704, 804, 904: projection
206, 306, 506, 706: substrate
211, 311, 711: projection undersurface
212, 312, 512, 712: membrane undersurface
514, 714: projection top
703, 805, 905: high-Young's modulus member 1001: ultrasonic diagnostic equipment
1002: ultrasonic probe
1003: transmitting/receiving separation unit
1004: transmission unit
1006: bias unit
1008: receiving unit
1010: phasing and summation unit
1012: image processing unit
1014: display unit
1016: control unit
1018: operation unit

The invention claimed is:

1. An ultrasonic transducer including a lower electrode, a hollow portion formed over the lower electrode and enclosed with an insulating film, an upper electrode formed over the hollow portion, and a plurality of projections of the insulating film formed in the hollow portion, comprising:
a plurality of rigid members formed over the hollow portion, wherein:
at least one of the lower electrode and upper electrode has portions thereof, which are layered over the projections of the insulating film, pierced, so that the electrode is located at a position at which the electrode is not layered over the projections of the insulating film when viewed from the upper surface; and the rigid members are disposed so that the rigid members are at least partially layered over the respective projections of the insulating film when viewed from the upper surface, and wherein the plurality of projections of the insulating film and the plurality of rigid members are equidistantly disposed when viewed from the upper surface.

2. The ultrasonic transducer according to claim 1, wherein: the rigid members are beam members; and a membrane including the insulating film, upper electrode, and beam members has a portion thereof, in which the beam members are disposed, made thicker than a portion thereof, in which the beam members are not disposed, by the thickness of the beam members.

3. The ultrasonic transducer according to claim 2, further comprising an upper insulating film formed to cover the upper electrode and hollow portion, wherein: the beam members are disposed over the upper insulating film.

4. The ultrasonic transducer according to claim 2, further comprising an upper insulating film formed to cover the upper electrode and hollow portion, wherein: the beam members are embedded in the upper insulating film.

5. The ultrasonic transducer according to claim 1, wherein the rigid members are members that exhibit a higher Young's modulus than the membrane including the insulating film, upper electrode, and beam members does.

6. The ultrasonic transducer according to claim 5, further comprising an upper insulating film formed to cover the upper electrode and hollow portion, wherein: the high-Young's modulus members are embedded in the upper insulating film.

7. The ultrasonic transducer according to claim 1, wherein the rigid members are disposed so that the centers of the rigid members coincide with the centers of the projections of the insulating film when viewed from the upper surface.

8. The ultrasonic transducer according to claim 1, wherein the rigid members are disposed so that one rigid member is layered over a plurality of projections of the insulating film.

9. The ultrasonic transducer according to claim 1, wherein the projections of the insulating film are disposed over the top of the hollow portion.

10. The ultrasonic transducer according to claim 1, wherein the projections of the insulating film are disposed over the bottom of the hollow portion.

11. The ultrasonic transducer according to claim 1, wherein one of the hollow portion is circular or polygonal when viewed from the upper surface, the projections of the insulating film are circular or polygonal when viewed from the upper surface, or the rigid members are circular, cruciform, or polygonal when viewed from the upper surface.

12. An ultrasonic diagnostic equipment comprising the ultrasonic transducer according to claim 1 and a bias unit.

13. An ultrasonic transducer including a lower electrode, a hollow portion formed over the lower electrode and enclosed with an insulating film, an upper electrode formed over the hollow portion, and a plurality of projections of the insulating film formed in the hollow portion, comprising:
a plurality of rigid members formed over the hollow portion, wherein:
at least one of the lower electrode and upper electrode has portions thereof, which are layered over the projections of the insulating film, pierced, so that the electrode is located at a position at which the electrode is not layered over the projections of the insulating film when viewed from the upper surface; and the rigid members are disposed so that the rigid members are at least partially layered over the respective projections of the insulating film when viewed from the upper surface, and wherein the rigid members are disposed so that one rigid member is layered over a plurality of projections of the insulating film.

14. The ultrasonic transducer according to claim 13, wherein: the rigid members are beam members; and a membrane including the insulating film, upper electrode, and beam members has a portion thereof, in which the beam members are disposed, made thicker than a portion thereof, in which the beam members are not disposed, by the thickness of the beam members.

15. The ultrasonic transducer according to claim 13, wherein one of the hollow portion is circular or polygonal when viewed from the upper surface, the projections of the insulating film are circular or polygonal when viewed from the upper surface, or the rigid members are circular, cruciform, or polygonal when viewed from the upper surface.

16. An ultrasonic diagnostic equipment comprising the ultrasonic transducer according to claim 13 and a bias unit.

17. An ultrasonic transducer including a lower electrode, a hollow portion formed over the lower electrode and enclosed with an insulating film, an upper electrode formed over the hollow portion, and a plurality of projections of the insulating film formed in the hollow portion, comprising:
a plurality of rigid members formed over the hollow portion, wherein:
at least one of the lower electrode and upper electrode has portions thereof, which are layered over the projections of the insulating film, pierced, so that the electrode is located at a position at which the electrode is not layered over the projections of the insulating film when viewed from the upper surface; and the rigid members are disposed so that the rigid members are at least partially layered over the respective projections of the insulating film when viewed from the upper surface, and wherein the rigid members are disposed so that the centers of the rigid members coincide with the centers of the projections of the insulating film when viewed from the upper surface.

18. The ultrasonic transducer according to claim 17, wherein: the rigid members are beam members; and a membrane including the insulating film, upper electrode, and beam members has a portion thereof, in which the beam members are disposed, made thicker than a portion thereof, in which the beam members are not disposed, by the thickness of the beam members.

19. The ultrasonic transducer according to claim 17, wherein one of the hollow portion is circular or polygonal when viewed from the upper surface, the projections of the insulating film are circular or polygonal when viewed from the upper surface, or the rigid members are circular, cruciform, or polygonal when viewed from the upper surface.

20. An ultrasonic diagnostic equipment comprising the ultrasonic transducer according to claim 17 and a bias unit.

* * * * *